United States Patent [19]

Tayag et al.

[11] Patent Number: 4,484,078
[45] Date of Patent: Nov. 20, 1984

[54] MEDICAL APPARATUS

[75] Inventors: Rolando Tayag, Benecia; George M. Menor, Martinez, both of Calif.

[73] Assignee: Siemens Medical Laboratories, Walnut Creek, Calif.

[21] Appl. No.: 404,466

[22] Filed: Aug. 2, 1982

[51] Int. Cl.³ .......................... G02B 5/00; H01J 29/46
[52] U.S. Cl. ................................. 250/505.1; 378/147
[58] Field of Search .......................... 250/492.3, 505.1; 378/117, 145, 147, 205

[56] References Cited

U.S. PATENT DOCUMENTS 1,600,867 9/1926 Coolidge .............................. 378/205
4,314,158 2/1982 Lucido .............................. 250/505.1

Primary Examiner—Bruce C. Anderson
Attorney, Agent, or Firm—Karl F. Milde, Jr.

[57] ABSTRACT

The apparatus comprises a first apparatus part and a second apparatus part which is disposed on and extends outward from the first part. The second part is movable with respect to the first part between an attracted position, in which it is extended to a predetermined extent, and a retracted position, in which it is extended to a lesser extent. The apparatus also comprises a security device disposed on at least one of the first and second parts. This device includes a magnetic device for exercising an attractive magnetic force between the first and second parts. Thereby the second apparatus part is maintained in the attracted position. It also includes a spring device for exercising an attractive mechanical force between the first and second parts. The mechanical force is comparatively low in the attracted position. It increases with increasing deviation from the attracted position towards the retracted position.

13 Claims, 8 Drawing Figures

MEDICAL APPARATUS

BACKGROUND OF THE INVENTION

1. Field of the Invention

This invention relates to a medical apparatus which contains a first apparatus part and a second apparatus part which is movable with respect to the first part. In particular, this invention relates to a security device for such a medical apparatus. Still more particularly, this invention relates to an electron applicator for a linear accelerator, or the like.

2. Description of the Prior Art

It is well known to use safety devices with medical apparatus which protect the patient, the operating personnel and the apparatus itself. Such a safety device is especially important in a medical apparatus in which a part extends towards the patient. In such an apparatus there exists the hazard that the patient may move unexpectedly and may hurt himself or herself by hitting against the protruding part.

Thus, it is desirable to have a safety device working in conjunction with the protruding apparatus part so that the patient will not get hurt in case he or she should inadvertently move against the extruding part.

In the field of linear accelerators, electron applicators having such safety feature are widely used. An electron applicator used in a linear accelerator determined for radiotherapy of patients is known from U.S. Pat. No. 4,314,158. This electron applicator is essentially an assembly of an outer or support tube and an inner or insert tube. The support tube is stationary and connected to the collimator of the linear accelerator. The upper portion of the insert tube is slidably mounted inside the support tube. Both tubes are preferably of cylindrical shape. A safety device is provided for preventing the insert tube from sliding out of the support tube. This safety device also engages the insert tube in a first working position when a treatment is performed. The safety device comprises a spring loaded pin extending through a hole in the wall of the support tube into an annular groove which is provided in the outer surface of the end portion of the insert tube. Upon a predetermined axial force, which may be inadvertently exercised by the patient under treatment, the insert tube slides back into the support tube.

In this electron applicator the actual force that has to be overcome in an emergency situation is primarily determined by the radial holding force, by the size and by the shape of the spring loaded pin. In addition, the principle of this safety device necessarily requires two tubes whereby the inner tube is slidably mounted in the outer tube. These features may result in some design restrictions.

SUMMARY OF THE INVENTION

1. Objects

It is an object of this invention to provide a safety device for a medical apparatus of the type having a first part and a second part, whereby the second part is movable with respect to the first part in response to an externally applied contact force.

It is another object of this invention to provide a safety device for a medical apparatus which safely operates even if the medical apparatus is operated upside-down.

It is still another object of this invention to provide a safety device for a medical apparatus which retracts when a patient or another person inadvertently touches it.

It is still another object of this invention to provide safety features for an electron applicator which can be applied upside-down, if desired.

It is still another object of this invention to provide a safety device which can be brought from an extended position into a safety or retracted position whereby initially a larger force has to be overcome than subsequently when the retracted position is approached.

It is still another object of this invention to design an electron applicator for a linear accelerator which applicator provides for good protection of the patient under treatment.

2. Summary

According to this invention, a medical apparatus contains a first and a second apparatus part which are movable with respect to each other. The second part is disposed on and extending outward from the first part. It is movable between an attracted position in which it is extended to a predetermined extent, and a retracted position in which it is extended to a lesser extent.

The medical apparatus also contains a security device which is disposed on one of the apparatus parts and which includes a magnetic device and a spring device. The magnetic device exercises an attractive magnetic force between the first and the second parts. Thereby the second apparatus part is maintained in the attracted position with respect to the first apparatus part. The spring device also exercises an attractive mechanical force between the first and second parts. This mechanical force is comparatively low in the attracted position and increases with increasing deviation from the attracted position when the second part moves towards the retractive position. In other words, the mechanical force increases with increasing distance from the attractive position.

In the attracted position, the attractive mechanical force is preferably much smaller than the attractive magnetic force. In this position, the attractive mechanical force may be zero.

The magnetic device may comprise one or more magnet buttons, a magnet ring arranged around a central axis, and the like, and a ferromagnetic piece such as a metal end plate which is attracted by the magnet(s) in the attracted position. The spring device may comprise a coil spring provided on a shaft or rod, a leaf spring, or another resilient element.

The foregoing and other objects, features and advantages of the invention will be apparent from the following more particular description of preferred embodiments of the invention as illustrated in the accompanying drawings.

DETAILED DESCRIPTION OF THE PREFERRED EMBODIMENTS

Figure 1:
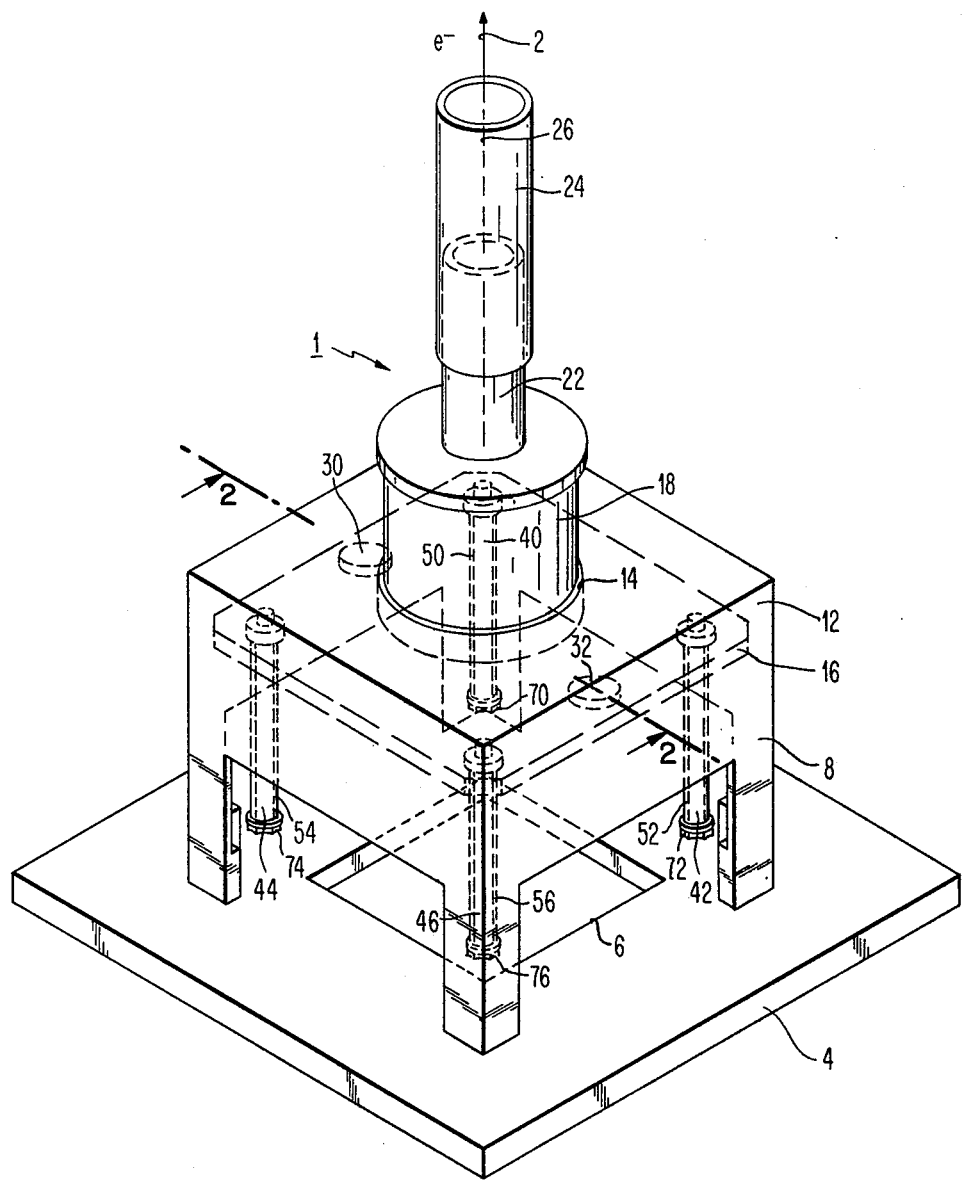
FIG. 1 is a perspective view of an electron applicator of a linear accelerator, according to the invention.

With reference to FIGS. 1-5, a medical system for application of radiation to a patient is provided. This medical system contains a medical apparatus, in particular an electron applicator 1, which will subsequently be described in more detail. The apparatus is used for application of electrons to the patient. The direction of the electrons is designated by an arrow 2. The apparatus works together with a linear accelerator as a source of high energy electrons. The electron applicator 1 is characterized by a specific security device for protection of the patient and the apparatus itself.

The electron applicator 1 comprises an attachment plate 4 which has a central aperture 6 for passage of electrons therethrough. The central aperture 6 is of rectangular shape.

In its middle section the attachment plate 4 supports a housing 8 which preferably may be made of a nonmagnetic material such as aluminum. The housing 8 is mounted on the attachment plate 4 by means of screws 10 (see FIG. 2). The housing 8 consists of four open side walls and a holding plate 12 on the upper end thereof. The thickness of the holding plate 12 is greater than the thickness of any of the four side walls. The holding plate 12 contains a central opening or first aperture 14 which is circular. The housing 8 including the four side walls and the holding plate 12 constitutes a first apparatus part. This first apparatus part is stationary as long as the electron applicator 1 in total is not rotated about the patient.

A second apparatus part is basically comprised of a rectangular end plate 16 and an adapter 18. The end plate 16 is located within the upper portion of the housing 8. It is attached in a fixed manner to the lower end of the adapter 18. The adapter 18 is essentially a tube which extends through the first aperture 14 and is slidably mounted therein. The central portion of the end plate 16 is provided with a circular central opening or second aperture 20. The aperture 20 admits high energy electrons into the second apparatus part. The space surrounded by the adapter 18 is a passageway for electrons. It is designated by 20. The adapter 18 may be replaced by another adapter having a different internal diameter and a different length.

Preferably the end plate 16 is made of a ferromagnetic material such as steel, whereas the cylindrical adapter 18 is preferably made of a nonmagnetic material such as aluminum.

Instead of rectangular plates 12 and 16, rings could be used.

The upper end of the adapter 18 supports a smaller tube 22.

This tube 22 is detachably connected to the adapter 18. The tube 22 may preferably be a steel tube. It is replaceable and may be exchanged by another tube 22 having a different internal diameter.

Attached to the upper end of the tube 22 is a sight tube 24. This sight tube 24 may preferably be made out of plastic. During the treatment of a patient, the upper end of the sight tube 24 is positioned close to the patient such that the electrons can easily reach the patient.

The central axis of the electron applicator 1 is denoted by 26. This axis 26 is determined by the apertures 6, 20 and the various tubes 18, 22, 24. The high energy electrons (see arrow 2) primarily travel along this central axis 26 and parallel thereto.

Figure 2:
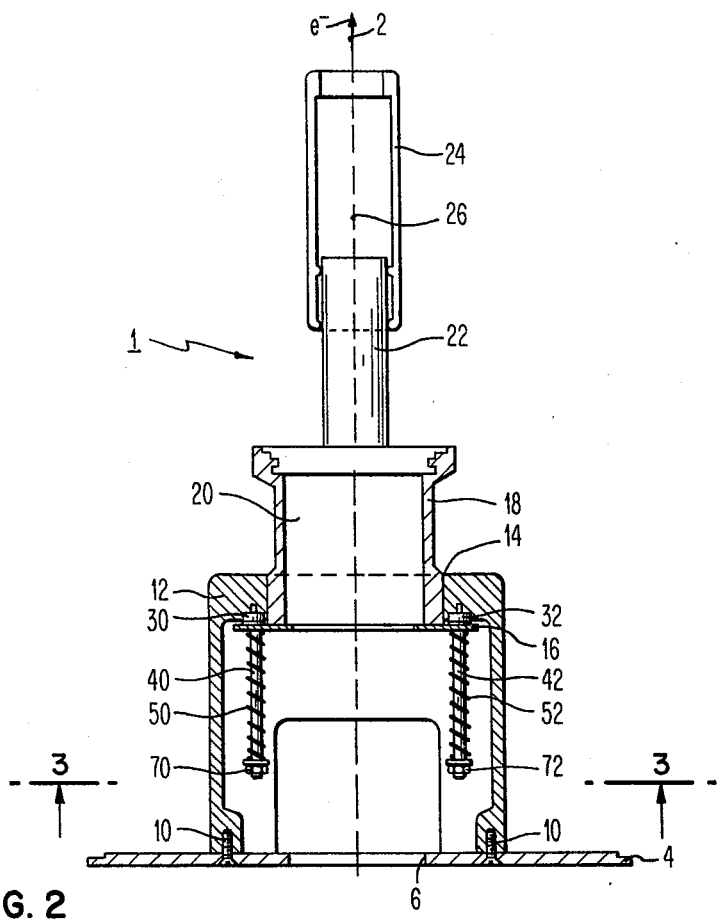
FIG. 2 is a cross-sectional side view of the electron applicator illustrated in FIG. 1.
Figure 3:
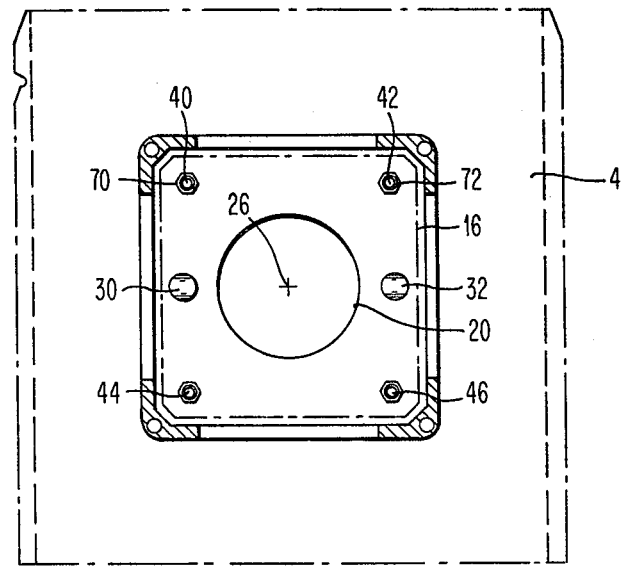
FIG. 3 is a plane view of the ferromagnetic end plate used in the electron applicator of FIGS. 1 and 2.

In a practical design of the illustrated electron applicator for use in conjunction with a linear accelerator, the weight of the adapter 18, the tube 22, the sight tube 24, and the end plates 16 may be considerable. In an actual design used for experimental purposes the weight of these four components was 5.5 lbs. Provision has to be made that in an upside-down position of the electron applicator 1 (as shown in FIGS. 1 and 2, where the electrons are emitted upward), the components 16, 18, 22 and 24 are supported in the illustrated extended position at any rate. Hereinafter, this extended position will be referred to as the "attracted position". In this position the second apparatus part is extended to a maximum extent.

In order to keep the second apparatus part 16, 18, 22, 24 in the attracted position, a security device including a magnetic device, ferromagnetic means, and a spring device is provided. This is illustrated on an extended scale in FIGS. 4 and 5.

The magnetic device exercises an attractive magnetic force between the stationary holding plate 12 and the movable end plate 16. It contains a first and a second magnet 30 and 32, respectively. These magnets 30, 32 are located in symmetrical positions around the central axis 26.

In particular, the lower surface of the holding plate 12 contains a first and a second recess 34 and 36, respectively. The magnets 30 and 32 are located in these recesses such that the lower surface of the plate 12 is flat. In particular, the magnets 30 and 32 are so-called button magnets, that is of cylindrical shape. Instead, a magnetic ring surrounding the central axis 26 could be used. Preferably, such a magnetic ring would be located in a central annular groove (not shown) provided in the lower surface of the holding plate 12.

The cylindrical magnets 30 and 32 are fixed in the recesses 34 and 36, respectively, by any known means, such as by screws, by bonding, etc.

Since the plate 16 is made of a ferromagnetic material, preferably of steel, the magnets 30 and 32 will atrract the end plate 16 towards the lower end of the holding plate 12, thereby extending the tube combination 18, 22, 24 to a maximum extent. In this attracted position, the upper side of the end plate 16 engages the lower end of the holding plate 12, and the upper end of the sight tube 24 is positioned close to the patient under treatment.

Provided close to the corners of the rectangular end plate 16 are four holes. The upper end of four pins or rods 40, 42, 44 and 46 is supported in each of these holes. The rods or pins 40-46 extend into the interior of the housing 8. On each rod 40, 42, 44 and 46 is located a coil spring 50, 52, 54 and 56, respectively. In FIGS. 1-5 only the coil springs 50 and 52 can be seen. The coil springs 50-56 are compression springs which may be biased in the aforementioned attracted position. The lower end of the rods 40-46 may support washers 60-66 which are secured thereupon by nuts 70-76. Thus, the coil springs 50-56 are kept in position by the end plate 16 on the upper end of the rods 40-46 and by the washers 60-66 at the lower end of the rods 40-46.

The function of the electron applicator 1 results in good protection of the patient in case he or she should inadvertently move against the upper end of the sight tube 24. Upon a predetermined axial force $F_0$ the second apparatus part 16, 18, 22 and 24 moves away from the patient, the tube 18 thereby sliding into the housing 8. This will be explained by means of FIG. 6.

Figure 6:
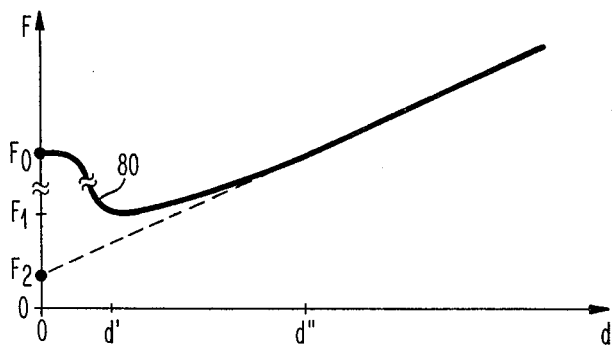
FIG. 6 is a diagram depicting the force S needed to be overcome in order to obtain the distance d between the stationary first apparatus part and the movable second apparatus part illustrated in FIGS. 4 and 5.

With reference to FIG. 6, a diagram depicting the axial force F in dependence on the distance d is illustrated. The force F is the force which the patient has to overcome should he or she inadvertently move against the end of the tube 24 of the applicator 1 in order to achieve a separation d between the end plate 16 and the holding plate 12.

At the beginning (d=0) of an emergency situation, that is in the attracted position, a comparatively large force $F_0$ is required before the two plates 12, 16 separate from each other. The force $F_0$ is the spring force and the magnetic force combined, if the coils 50-56 are biased. However, the magnetic force is larger than the spring force, i.e. the force $F_0$ is basically determined by the holding force of the magnets 30, 32. The force $F_0$ must be large enough to carry the weight of the movable components (for in some medical applications the applicator is positioned upside down, as specified earlier).

After the force $F_0$ has been overcome and a separation has taken place, the tube assembly easily slides back. Now a decreasing force F is required to achieve a larger separation distance d. The magnetic attractive force sharply decreases with increasing distance d. This is indicated in FIG. 6 by the sharp decline 80 of the illustrated curve.

At a certain distance d', only a minimum force $F_1$ is necessary to keep the assembly 16, 18, 22, 24 in their momentary position. The minimum force $F_1$ is much smaller than the initial force $F_0$. From this point on, one can obtain an increased separation distance d only by increasing the force F. But this force F is still comparatively small. Starting at a distance d", the force F required to push back the assembly is linearly dependent on the distance d. In this region, the force F is basically determined by the number and the nature of the applied springs 50-56. The force F may be chosen to slowly increase with the distance d. That is, small spring rates may be selected.

With respect to the linear curve portion, it should be mentioned that the design parameters were selected such that at a distance d=0 a small force $F_2$ would have to be overcome even if the magnets 30, 32 were not present. In other words, the springs 50-56 are biased so as to exercise a joining force.

In the aforementioned test design (weight 5.5 lbs.) the predetermined force $F_0$ to be overcome in the attracted position (d=0) was chosen as 8 to 10 lbs., whereas the minimum $F_1$ was chosen as 2 lbs. That is, the patient only has to exercise a minimum force $F_1=2$ lbs. in order to further push back the applicator after the initial magnetic force $F_0$ has been overcome. For the linear portion of the curve in FIG. 6, a spring rate of 1.88 lbs/inch was selected for each of the four spring coils 50-56.

Figure 7:
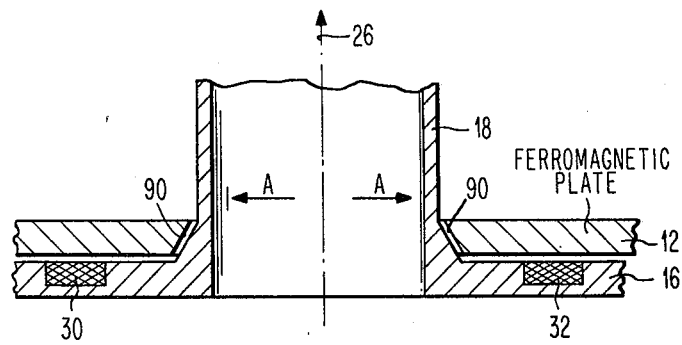
FIG. 7 is a partial cross-sectional side view of a modification of the end plate and hold plate illustrated in FIGS. 1-5.

In FIG. 7 an embodiment is illustrated in which the holding plate 12 is provided with oblique corners 90. Correspondingly oblique rims are provided on the tubes 18. This serves two purposes: It makes the positioning of the adapter 18 easy, and it generates a kind of holding force A between the holding plate 12 and the end plate 16. In this embodiment, the holding plate 12 is a ferromagnetic plate or ring. Consequently, the button magnets 30 and 32 are fixed in recesses provided in the upper surface of the end plate 16.

Figure 8:
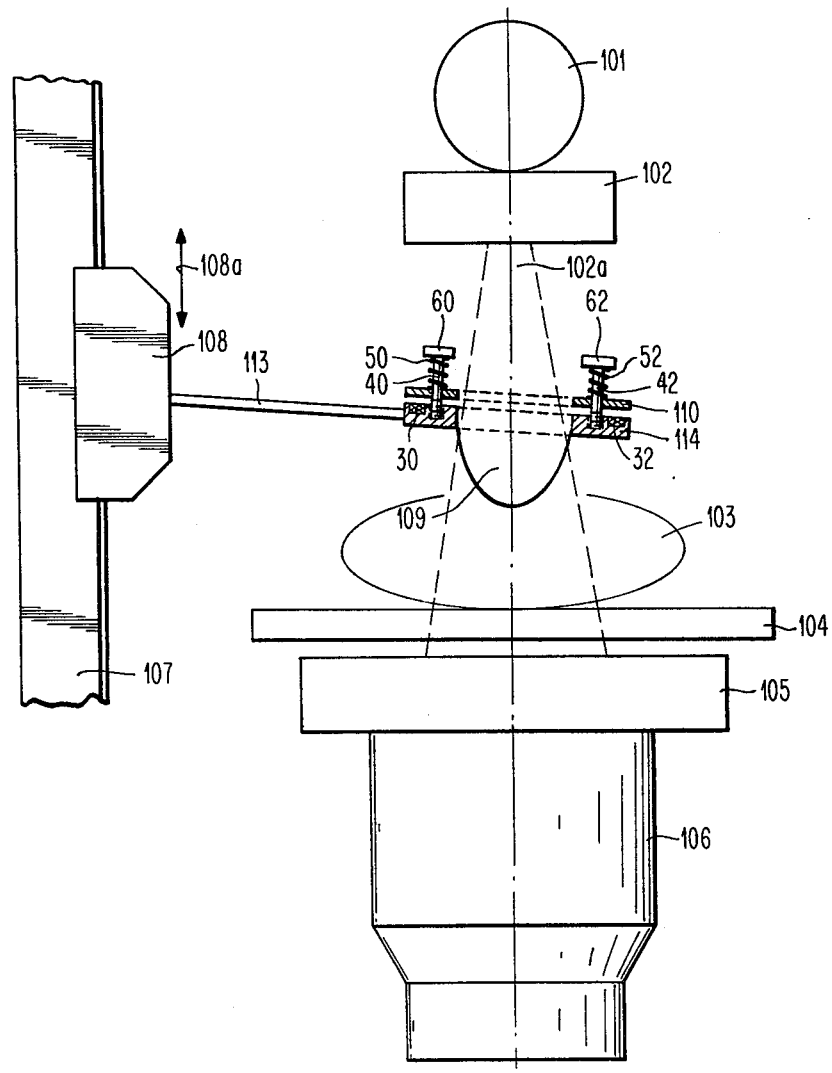
FIG. 8 is a schematic diagram of an X-ray examination apparatus containing a safety device for the compression cone thereof, according to the invention.

In FIG. 8 an X-ray examination apparatus containing a safety device according to the invention is illustrated. This safety device is determined for the compression cone 109 of the X-ray apparatus.

The X-ray examination apparatus is widely of conventional design. It comprises an X-ray tube 101, and a primary collimator 102 for selecting an X-ray cone 102a which is emitted towards a patient 103. The patient 103 is supported by a patient table 104. Underneath the table 104 is located an imaging device 105 including an image intensifier and television monitor unit 106.

A tubular support 107 is provided for carrying a carriage 108 which is movable therealong (see double arrow 108a). A carrier arm 113 extends from the carriage 108. The arm 113 supports a ring flange 114 which has provided on its upper surface a certain number of recesses. In each recess is located a magnet 30, 32. The flange 114 is made out of a nonferromagnetic material.

Opposite the flange 114 is positioned a flange 110 which supports the compression cone 109. This flange 110 may be a ring. It is made of a ferromagnetic material.

Figure 4:
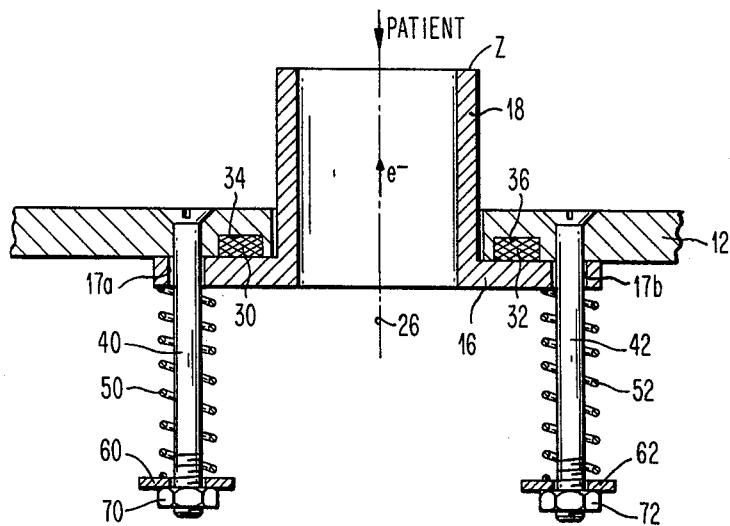
FIG. 4 is a partial cross-sectional side view of the electron applicator of FIGS. 1-3 in its attracted position.
Figure 5:
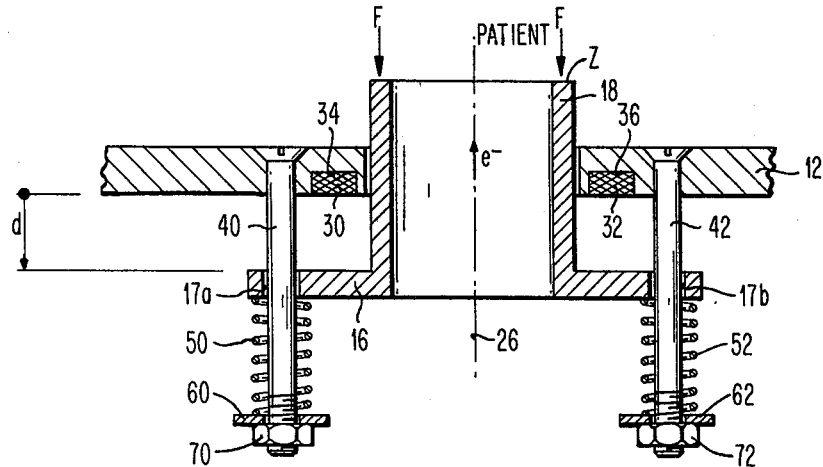
FIG. 5 is a partial cross-sectional side view of the electron applicator of FIGS. 1-3 in its retracted position.

In accordance with FIGS. 4 and 5, the flange 114 supports pins 40 and 42 which extend upward. These pins 40 and 42 are guided through apertures in the flange 110, which is in correspondence with FIGS. 4 and 5. The upper ends of the pins 40, 42 are provided with end pieces or washers 60, 62, respectively. Inbetween, coil springs 50, 52 are provided.

If the patient 103 contacts the compression cone 109 with a force greater than $F_0$, the flange 110 supporting the cone 109 will slide along the pins 40, 42 in an upward direction.

While the forms of the medical apparatus herein described constitute preferred embodiments of the invention, it is to be understood that the invention is not limited to these precise forms of assembly, and that a variety of changes may be made therein without departing from the scope of the invention.

What is claimed is:

1. A medical apparatus for application of radiation to a patient, comprising in combination:
   (a) a housing having an aperture;
   (b) a tube enclosing a passageway for the radiation and being disposed on and extending outward from said aperture of said housing, said tube being movable with respect to said housing between an attracted position, in which said tube is extended to a predetermined extent and a retracted position, in which said tube is extended to a lesser extent; and
   (c) a security device disposed on at least one of said housing and tube, including
      (c1) magnetic means for exercising an attractive magnetic force between said housing and tube, said tube thereby being maintained in said attracted position with respect to said housing; and
      (c2) spring means for exercising an attractive mechanical force between said housing and tube, said mechanical force in comparison with the attractive magnetic force of said magnetic means being low in said attracted position and increasing with increasing deviation from said attracted position towards said retracted position;

said security device being designated for the protection of the patient in case the patient moves against the tube, thereby, after having overcome the attractive magnetic force of the magnetic means moving the tube into the retracted position against the initially low mechanical force of the spring means.

2. The medical apparatus according to claim 1, wherein said housing and tube are located around a central axis, said central axis extending through said aperture of the housing and the passageway of the tube.

3. The medical apparatus according to claim 2, wherein said magnetic means are equally distributed around said central axis.

4. The medical apparatus according to claim 1, wherein said magnetic means comprises a plurality of button magnets.

5. The medical apparatus according to claim 1, wherein said magnetic means is a magnetic ring.

6. The medical apparatus according to claim 1, wherein said housing contains a recess in its surface, and wherein said magnetic means is located in said recess.

7. The medical apparatus according to claim 6, wherein said tube comprises a ferromagnetic material.

8. The medical apparatus according to claim 2, wherein
    (a) said housing comprises a holding plate having said aperture located in the center thereof around the central axis, and
    (b) said tube comprises an end plate having said passageway located in the center thereof around the central axis.

9. The medical apparatus according to claim 8, wherein said magnetic means is located between said holding plate and said end plate, and wherein one of said plates contains a ferromagnetic material.

10. The medical apparatus according to claim 1, wherein said spring means comprises a rod and a coil spring, said coil spring being loated on said rod.

11. The medical apparatus according to claim 10, wherein said coil spring is a compression spring, and wherein said compression spring is biased in said attracted position.

12. The medical apparatus according to claim 10, wherein one end of said rod is connected to one of said housing and tube, and wherein a washer is provided on a second end of said rod.

13. The medical apparatus according to claim 1, wherein an exchangable end piece is connected to said tube, said exchangable end piece being determined for being approached to a patient.

* * * * *